(12) United States Patent
Hasenwinkel et al.

(10) Patent No.: US 8,575,274 B2
(45) Date of Patent: *Nov. 5, 2013

(54) MULTI-SOLUTION BONE CEMENTS AND METHODS OF MAKING THE SAME

(75) Inventors: Julie M. Hasenwinkel, Manlius, NY (US); Imad K. Merkhan, Warsaw, IN (US); Jeremy L. Gilbert, Fayetteville, NY (US)

(73) Assignee: Syracuse University, Syracuse, NY (US)

( * ) Notice: Subject to any disclaimer, the term of this patent is extended or adjusted under 35 U.S.C. 154(b) by 691 days.

This patent is subject to a terminal disclaimer.

(21) Appl. No.: 11/779,025

(22) Filed: Jul. 17, 2007

(65) Prior Publication Data

US 2008/0039586 A1 Feb. 14, 2008

Related U.S. Application Data

(60) Provisional application No. 60/807,551, filed on Jul. 17, 2006.

(51) Int. Cl.
*C08F 8/00* (2006.01)

(52) U.S. Cl.
USPC ........... 525/228; 525/902; 525/259; 525/261; 525/330.3; 525/330.5; 525/330.6; 525/302; 523/117; 523/116; 523/115

(58) Field of Classification Search
USPC ........... 523/117, 116, 115; 525/88, 228, 902, 525/259, 261, 330.3, 330.5, 330.6, 302
See application file for complete search history.

(56) References Cited

U.S. PATENT DOCUMENTS

| | | | | |
|---|---|---|---|---|
| 3,928,499 A | * | 12/1975 | Tomalia et al. | 525/296 |
| 4,396,476 A | * | 8/1983 | Roemer et al. | 522/109 |
| 4,791,150 A | | 12/1988 | Braden et al. | |
| 4,969,888 A | * | 11/1990 | Scholten et al. | 606/94 |
| 5,334,626 A | | 8/1994 | Lin | |
| 5,728,583 A | * | 3/1998 | Kawakami et al. | 436/69 |
| 5,902,839 A | * | 5/1999 | Lautenschlager et al. | 523/115 |
| 6,709,149 B1 | * | 3/2004 | Tepic | 366/139 |
| 2004/0220297 A1 | | 11/2004 | Bonfield et al. | |
| 2009/0239970 A1 | | 9/2009 | Rodrigues | |
| 2010/0273911 A1 | | 10/2010 | Hasenwinkel | |

FOREIGN PATENT DOCUMENTS

| | | |
|---|---|---|
| WO | WO9824398 A1 | 6/1998 |
| WO | WO2006090379 A1 | 8/2006 |

OTHER PUBLICATIONS

Vallo et al. J. Biomed. Mater. Res. 2003, 70B, 407.*
Jayachandran et al. European Polymer Journal 2000, 36, 743-749.*

(Continued)

*Primary Examiner* — Mark Kaucher
(74) *Attorney, Agent, or Firm* — Frederick J. M. Price; Bond Schoeneck & King, PLLC

(57) ABSTRACT

The present invention relates to bone cements and, more particularly, to multi-solution bone cements and methods for making the same. An embodiment of the present invention provides multi-solution bone cements which include cross-linked PMMA beads, thereby providing for a significant increase in the polymer-to-monomer (P:M) ratio. Another embodiment of the present invention provides cross-linked PMMA beads which are surface modified with unsaturated carbon double bonds. A further embodiment of the present invention provides multi-solution bone cements made with PMMA-PMMA spherical brush polymers.

9 Claims, 6 Drawing Sheets

(56) References Cited

OTHER PUBLICATIONS

C.I. Vallo et al. "Influence of cross-linked PMMA beads on the mechanical behavior of self-curing acrylic cements", Journal of Biomedical Materials Research. Part B: Applied Biomaterials, 2004, vol. 70B, No. 2, pp. 407-416, See the abstract.

Hernandez, et al., Influence of powder particle size distribution on complex viscosity and other properties of acrylic bone cement for vertebroplasty and kyphosplasty, J Biomed Mater Res B; Appl Biomater 2006, vol. 77(B), pp. 98-103.

Borukhov I and Leibler L, Enthalic stabilization of brush coated particles in a polymer melt, Macromolecules 2002; 35: 5171-5182.

Lin EK and Gast AP, Self consistent field calculations of interactions between chains tethered to spherical interfaces. Macromolecules 1996; 29: 390-297.

Lewis, Alternative acrylic bone cement formulations for cemented arthroplasties: present status, key issues, and fracture prospects. J Biomed Mater Res B: Appl Biomater 2008, vol. 84B, pp. 301-319.

Lewis, Injectable bone cements for use in vertebroplasty and kyphoplasty: state-of-art-review. J Biomed Mater Res B: Appl Biomater 2006, vol. 76B, pp. 456-468.

Lieberman, et al., Vertebroplasty and Kyphoplasty: filler materials, Spine J 2005, vol. 5, pp. 305S-316S.

Jarvik, et al., Vertebroplasty: Learning more, but not enough. Spine 2003, vol. 28(14), pp. 1487-1489.

Belkoff, et al., Temperature measurement during polymerization of polymethylmethacrylate cement used for vertebroplasty, Spine 2003, vol. 28(14), pp. 1555-1559.

Belkoff, et al., The biomechanics of vertebroplasty. The effect of cement volume on mechanical behavior, Spine 2001, vol. 26(14), pp. 1537-1541.

Molloy, et al., Effect of cement volume and placement on mechanical property restoration resulting from vertebroplasty, AJNR Am J Neuroradiol 2005, vol. 26, pp. 401-404.

Phillips, Minimally invasive treatments of osteoporotic vertebral compression fractures, Spine 2003, vol. 28, pp. S45-S53.

Deb, et al., The effect of cross-linking agents on acrylic bone cements containing radiopacifiers, Biomaterials 2001, vol. 22, pp. 2177-2181.

Jasper, et al., Material properties of various cements for use with vertebroplasty, J Mater Sci, Mater Med 2002, vol. 13, pp. 1-5.

Lewis, et al., Influence of the radiopacifier in an acrylic bone cement on its mechanical, thermal, and physical properties: Barium sulfate containing cement versus iodine-containing cement, J Biomed Mater Res B, Appl Biomater 2005, vol. 73B, pp. 77-87.

Van Hooy-Corstjens, et al., Mechanical behavior of a new acrylic radiopaque iodine-containing bone cement, Biomaterials 2004, vol. 25, pp. 2657-2667.

Kurtz, et al., Static and fatigue mechanical behavior of bone cement with elevated barium sulfate content for treatment of vertebral compression fractures, Biomaterials 2005 vol. 26, pp. 3699-3712.

Ginebra, et al., Mechanical performance of acrylic bone cements containing different radiopacifying agents, Biomaterials 23, 2002, pp. 1873-1882.

Ruckenstein, Eli and Chung, Dennis Byungip, Surface Modification by a Two-Liquid Process Deposition of A-B Block Copolymers, Department of Chemical Engineering, State University of New York, Buffalo, NY, pp. 170-185, Date: 1988.

Wang, et al., Fracture toughness of acrylic bone cements, J Mater Science 1989, vol. 24, pp. 3725-3738.

Vallo, et al. Mechanical and fracture behavior evaluation of commercial acrylic bone cements, Polym Int 1997, vol. 43, pp. 260-268.

Persson, et al., Radiopacity of tantalum-loaded acrylic bone cement, Proc I Mech E 2006, vol. 220, pp. 787-791.

Hasenwinkel, et al., A novel high-viscosity, two-solution acrylic bone cement: effect of chemical composition on properties, J. Biomed Mater Res 1999, vol. 47, pp. 36-45.

Hasenwinkel, et al., Effect of initiation chemistry on the fracture toughness, fatigue strength, and residual monomer content of a novel high-viscosity, two solution acrylic bone cement, J Biomedical Materials Research 2002, vol. 59, pp. 411-421.

ASTM F451-99a, 2007el, "Standard Specification for Acrylic Bone Cement", ASTM International, West Conshohocken, PA, www.astm.org.

Kjellson, et al., Bone cement X-ray contrast media: A clinically relevant method of measuring their efficiency, J Biomed Mater Res B: Appl Biomater 2004, vol. 70B, pp. 354-361.

Pascual. et al., New aspects of the effect of size and size distribution on the setting parameters and mechanical properties of acrylic bone cements, Biomaterials 1996, vol. 127, pp. 509-516.

Sun, et al., Model filled polymers. VII: Flow behavior of polymers containing monodisperse crosslinked polymeric beads. Polym Eng Sci 1992, vol. 32(12), pp. 777-785.

Li, et al. Model filled Polymers: The effect of particle size on the theology of filled poly(metyl methacrylate) composites. Polym Eng Sci 2004, vol. 44, pp. 452-462.

Miller, S.T., Polymer Brushes, Science, New Series, vol. 251, No. 4996 (Feb. 22, 1991), pp. 905-914.

Burton, et al., Vertebroplasty and Kyphoplasty: a compressive review, Neurosurg Focus 2005, vol. 18(3), pp. 1-7.

Lewis, Properties of acrylic bone cements: State of the art review, J Biomed Mater Res B: appl Biomater 1997, vol. 38B, pp. 155-182.

Verlan, et al., Temperature elevation after vertebroplasty with polymethyl-methacrylate in the goat spine, J Biomed Mater Res B: Appl Biomater 2003, vol. 67B, pp. 581-585.

Hass, et al., A characterization of polymethylmethacrylate bone cement, J Bone Joint Surg A 1975, vol. 57, pp. 380-391.

Meyer, et al., On the settling properties of acrylic bone cement, J Bone Joint Surg A 1973, vol. 55, pp. 149-156.

Krause, et al., The viscosity of acrylic bone cements, J Biomed Mater Res 1982, vol. 16, pp. 219-243.

Chaffey, et al., Shear thinning and thickening rheology II, Volume fraction and size of dispersed particles, J Col Interf Sci 1977, vol. 59(I), pp. 63-75.

Probstein, et al., Bimodal model of concentrated suspension viscosity for distributed particle sizes, J Rheol 1994, vol. 38(4), pp. 811-829.

* cited by examiner

MULTI-SOLUTION BONE CEMENTS AND METHODS OF MAKING THE SAME

CROSS REFERENCE TO RELATED APPLICATIONS

The present application claims priority to U.S. Provisional Application No. 60/807,551, filed on Jul. 17, 2006.

BACKGROUND OF THE INVENTION

1. Field of the Invention

The present invention relates to bone cements and, more particularly, to multi-solution bone cements and methods for making the same.

2. Description of the Related Art

The clinical use of total joint replacements in the United States is expected to rise precipitously over the next twenty-five years, projected to the level of over 4 million primary total knee and hip replacement procedures performed annually by the year 2030. The number of revision surgeries for both total hips and total knees will likely double over this time period as well. Thus, the demand for high performance bone cement is rapidly growing.

One of the critical factors in the clinical success of total joint arthroplasty is stable fixation of the prosthesis; which, in a majority of cases, is accomplished through the application of PMMA-based bone cement. While bone cement has been used clinically since the early 1960's and there are many commercially available powder-liquid cement compositions, the material continues to be scrutinized for the role that it plays in aseptic loosening of total joint prostheses.

Multi-solution acrylic bone cements (typically referred to as a two-solution bone cement, but which could have more than two solutions) have surfaced as an alternative to powder-liquid cement, using the same chemical constituents as current commercial formulations. This cement consists of PMMA powder pre-dissolved in methyl methacrylate (MMA) monomer, to form two separate solutions; one containing the initiator, benzoyl peroxide (BPO) and the other containing the activator, N,N-dimethyl-p-toluidine (DMPT), which react to initiate polymerization of the MMA when the solutions are mixed. These solutions have an initial viscosity similar to that of powder-liquid cement in the dough stage, therefore they can be simultaneously mixed and delivered to the surgical site via a single, closed system. This not only simplifies the surgical procedure by eliminating the multi-stage process of cement mixing and delivery, but also reduces the extent to which the properties of the polymerized cement depend on variations in surgical technique. Two-solution bone cement compares favorably to commercial cements (Simplex P and Palacos R) both in its mechanical properties and biocompatibility.

While the two-solution bone cement concept is a promising alternative to powder-liquid cements, it has several drawbacks in its current form, primarily related to the increase in monomer concentration necessary to form viscous solutions of dissolved linear PMMA. Many important properties of the cement, including the polymerization exotherm, residual monomer concentration, volumetric shrinkage, and shrinkage-induced porosity, are directly proportional to the initial monomer concentration. These properties represent the key areas where two-solution cement currently does not perform as well as commercial powder-liquid cements. The reduction of monomer in two-solution bone cement is limited by the solution viscosity, which is controlled by both the concentration and molecular weight (MW) of the PMMA in solution. Increasing the P:M ratio, without decreasing the MW of the PMMA, increases solution viscosity, yielding cements, which are difficult to mix and deliver. Significantly decreasing the PMMA MW in order to increase the P:M ratio, however, leads to a marked decrease in the mechanical properties of the polymerized cement.

SUMMARY OF THE INVENTION

It is therefore a principal object and advantage of the present invention to provide a multi-solution bone cement incorporating more PMMA.

It is another object and advantage of the present invention to provide a multi-solution bone cement having improved mechanical properties.

In accordance with the foregoing objects and advantages, an embodiment of the present invention provides multi-solution bone cements which include cross-linked PMMA beads, thereby providing for a significant increase in the polymer-to-monomer (P:M) ratio. As a result, the bone cements of the present invention have reduced polymerization exotherms, volumetric shrinkage, shrinkage induced porosity, and residual monomer, all of which are advantageous for the clinical performance of the cement. When surface modified with unsaturated carbon double bonds, the cross-linked PMMA beads exhibit improved interfacial adhesion between the beads and the polymerized cement matrix by allowing them to participate in the polymerization reaction and thus be covalently bound to the matrix, thereby improving the mechanical properties of cements made with functionalized beads. One advantage of the multi-solution bone cements of the present invention is the ability to adjust viscosity by means of the P:M ratio and the ratio of cross-linked beads to linear polymer in the composition.

In accordance with an embodiment of the present invention, the present invention also comprises multi-solution bone cements made with PMMA-PMMA spherical brush polymers. The density and molecular weight of PMMA chains grafted onto cross-linked PMMA beads are controlled through the atom transfer radical polymerization process, along with the concentration of these particles in the monomer solutions, thereby enabling the manufacture of bone cements with tailored viscosities.

As noted supra, multi-solution bone cements consist of linear polymer chains consisting of acrylate (e.g., PMMA) polymer dissolved into MMA monomer. The viscosity of these cements is dictated by the combination of polymer molecular weight and polymer-to-monomer ratio. Increasing either of these quantities will increase the viscosity. In order to obtain workable cement viscosities, the combination of suitable molecular weight and polymer to monomer ratio are typically in the 80,000 g/mol lower limit Mw and about 0.95:1 polymer-to-monomer ratio. Since typical powder liquid cements are in the range of 1.8:1 P:M ratio, changes in two solution cement are needed to raise the P:M ratio while still preserving suitable viscosity.

In accordance with an embodiment of the present invention, modified multi-solution cements contain an additional element that can comprise either cross-linked PMMA beads or reactive cross-linked beads (where reactive double bond groups are placed on the surface of the beads) that are added to the multi solution mixture. The amount of crosslinking within the beads, the ratio of linear polymer (Pl) to bead-based polymer (Pb), and the bead size will all affect the viscosity of the mixture. Furthermore, varying crosslinking concentration (i.e., the amount of crosslinking agent used to create the cross-linked PMMA beads—e.g., EGDMA) within the polymer beads will affect the amount of monomer uptake and swelling that can take place within the beads which will, in turn, affect the overall viscosity of the system. Additionally, cements can be made by the addition of spherical polymer brushes alone to MMA.

In addition to the advantages previously described, the bone cements of an embodiment of the present invention are significantly simpler for the surgeon to mix and apply in the operating room compared to current powder-liquid bone cements. Simplification of this process eliminates much of the technique-dependent variability in bone cement properties. Additionally, the polymerization of multi-solution based bone cements is initiated by mixing the two or more components through a static mixing nozzle (current design) or some comparable device. The cement can be simultaneously mixed and delivered to the surgical site of application if desired. The use of a disposable mixing nozzle allows for metered dosing from a single batch of cement. For example, a desired volume of material can be mixed and delivered in order to cement the first component of a total knee replacement. The mixing nozzle can then be removed and at the appropriate time, a new nozzle can be attached to mix the cement for the second component of the knee implant. The flexibility that this type of approach affords the surgeon is highly advantageous from a delivery standpoint because it allows for multiple cement applications at different times during a single surgical procedure, from a single batch or dose of cement. This type of approach is not possible with conventional bone cements because an entire batch must be mixed at one time, thus starting the polymerization reaction and limiting the time with which the surgeon can work with the cement before it cures. Bone cements of different viscosities are desirable for different surgical procedures (e.g., khyphoplasty vs. total hip cementation vs. total knee cementation). The ability to customize cements for the various market niches within the field of orthopedics is therefore highly desirable.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
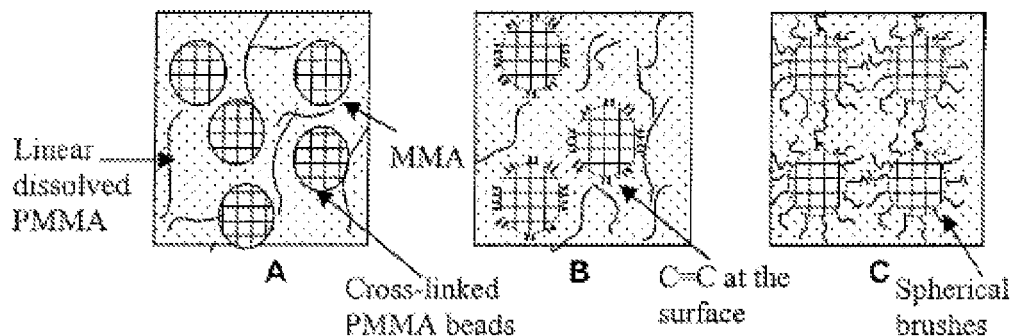
FIG. 1 is a schematic of three bone cement systems according to an embodiment of the present invention.

Referring now to the drawings, wherein like reference numerals refer to like parts throughout, there is seen in FIG. 1 (FIG. 1A-C) three cement systems according to the present invention. Briefly, FIG. 1(A) shows linear polymer and cross-linked beads in monomer, FIG. 1(B) shows linear polymer, and C=C modified cross-linked beads in monomer, and FIG. 1(C) shows polymer brushes in monomer.

An embodiment of the present invention generally comprises multi-solution based bone cements having polymer-to-monomer (P:M) ratios approaching 2:1 and material properties that are comparable to currently available powder-liquid cements.

In accordance with an embodiment of the present invention, the viscosity of the cement solutions of the present invention are a function of the total P:M ratio, the ratio of cross-linked beads to linear polymer, and the cross-link density and size of the beads. The bone cements of an embodiment of the present invention are formed by adding polymer in the form of cross-linked poly(methyl methacrylate) (PMMA) beads to solutions of dissolved linear polymer. Alternatively, the present invention is formed by replacing the linear polymer with spherical PMMA brushes. Cross-linked PMMA particles swell in monomer but do not dissolve, minimizing their contribution to the viscosity of the polymer solutions compared to the dissolved linear polymer.

An embodiment of the present invention involves the enhancement of the interfacial bonding of this particle phase to the polymerized PMMA matrix, and subsequently the mechanical properties of the cement, by creating reactive sites at the surface of the cross-linked beads that could participate in the free radical polymerization reaction during cement curing.

An embodiment of the present invention also encompasses the synthesis of spherical polymer brushes, consisting of cross-linked PMMA beads with linear PMMA molecules covalently tethered to their surfaces. The spherical PMMA are mixed with methyl methacrylate (MMA) monomer to create bone cement formulations which do not required additional dissolved linear PMMA. In the presence of the monomer, the cross-linked bead component of the spherical brushes will swell and the tethered PMMA chains will act like dissolved polymer, although anchored at one end, thereby imparting both viscosity to the mixtures through physical chain entanglements and a mechanically coupled interface at the surface of the beads.

In accordance with an embodiment of the present invention, plain cross-linked PMMA beads can be used in combination with dissolved linear PMMA in methyl methacrylate monomer (MMA) to form the first cement type, as seen in FIG. 1(A).

In accordance with an embodiment of the present invention, the cross-linked PMMA beads can be modified via chemical reaction, in order to create functional reactive sites at the surface of the beads, consisting of carbon-carbon double bonds. These bonds will be able to participate in the free radical polymerization reaction that occurs during bone cement setting, creating a covalent or chemical bond between the cross-linked beads and the polymerized cement matrix. These cross-linked PMMA beads can be used in combination with dissolved linear PMMA in MMA monomer to form the second cement type, as seen in FIG. 1(B). Using functionalized beads in this cement composition improves interfacial bonding between the particle phase and the polymerized PMMA matrix, resulting in cements with enhanced mechanical properties.

In accordance with an embodiment of the present invention, the last cement type is based on the synthesis of spherical polymer brushes, consisting of cross-linked PMMA beads with linear PMMA molecules covalently tethered to their surfaces. Spherical PMMA brushes are then be mixed with methyl methacrylate (MMA) monomer to create the third cement type, as seen in FIG. 1(C). This cement composition does not require additional dissolved linear PMMA. In the presence of the monomer, the cross-linked bead component of the spherical brushes will swell and the tethered PMMA chains will act like dissolved polymer, although anchored at one end, thereby imparting both viscosity to the mixture through physical chain entanglements and a mechanically coupled interface at the surface of the beads.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

EXAMPLES

Example 1

Synthesis of Cross-Linked PMMA Beads

This example relates to the synthesis of cross-linked PMMA beads. In brief, cross-linked PMMA beads have been synthesized via suspension polymerization of methyl methacrylate, using benzoyl peroxide (BPO), 2,2'-azo-bis-isobutyrylnitrile (AIBN), or potassium persulfate (KPS) as the initiator, ethylene glycol dimethacrylate (EGDMA) as the cross-linker (in varying concentrations), and poly(vinyl alcohol) (PVA) as the stabilizer. Resulting beads were subjected to post-synthesis heat treatment at 91° C. for 18 h in order to decompose any residual BPO and yield polymer that is stable in monomer solutions containing DMPT. Bead size can be controlled by varying the suspension medium and the speed of mixing during the synthesis. Beads that have been synthesized to date range in size from less than 1 µm to over 100 µm in diameter, with the majority in the 10-50 µm range. Cross-linker concentrations have been varied between 1% and 30%. The degree to which the beads swell in monomer solutions is inversely proportional to the cross-linker concentration used in the synthesis.

Example 2

Preparation of Multi-Solution Based Bone Cement with Cross-Linked PMMA Beads This example relates to the preparation of multi-solution based bone cement with cross-linked PMMA beads as synthesized in Example 1. First, the desired ratio of cross-linked beads to PMMA powder (linear chains) is determined. These two components are massed and subsequently mixed together in a suitable container. Next, MMA is added to two graduated cylinders. The desired concentrations of BPO initiator or DMPT activator are then dissolved in MMA in separate containers, followed by the addition of 10-30 wt % barium sulfate (if radiopacity is desired, e.g., for vertebroplasty and kyphoplasty applications). The solutions are transferred to polypropylene cartridges. Next, the mixture of PMMA powder and cross-linked PMMA beads is added to the MMA solutions. The cartridges are sealed, vigorously agitated by hand, and placed on a rotating drum mixer for 6 hours. This is a significant reduction in mixing time as compared to current two-solution cement formulations without cross-linked beads (18 hr). Following mixing, the cartridges are removed and stored upright at 4° C. The solutions can be mixed through a static mixing nozzle and polymerize in the same manner as two-solution bone cement without cross-linked beads.

Example 3

Figure 2:
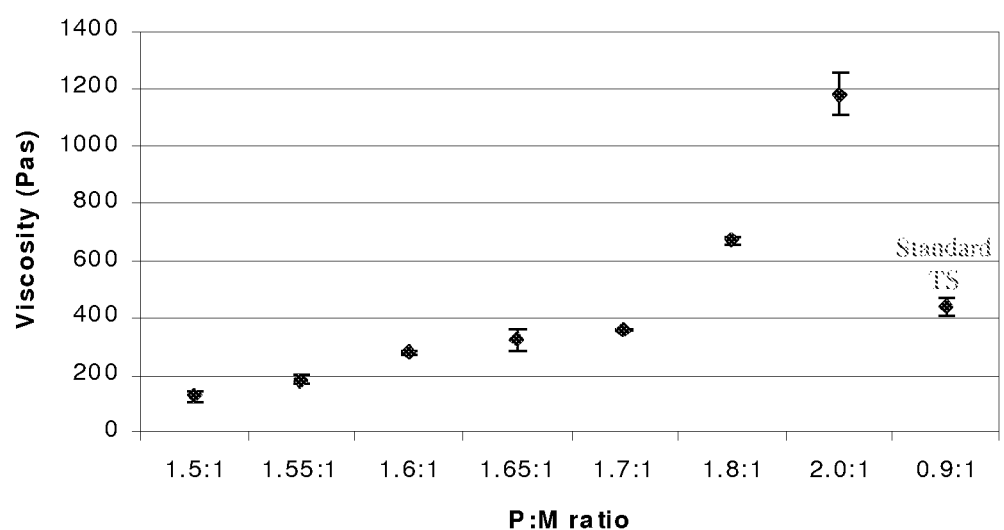
FIG. 2 is a graph of viscosity versus polymer-to-monomer ratios for multi-solution bone cements according to an embodiment of the present invention.

Properties of Multi-Solution Based Bone Cement with Cross-Linked PMMA Beads This example relates to the properties of the multi solution based bone cement with cross-linked PMMA beads as described in Example 2. A number of experiments have been performed to characterize the properties of solutions and potential cement compositions of multi-solution based bone cement with cross-linked PMMA beads. The viscosity of solutions consisting of cross-linked PMMA beads, linear PMMA, and MMA, increase significantly with increasing polymer-to-monomer (P:M) ratio, as seen in FIG. 2. FIG. 2 depicts the viscosity versus polymer-to-monomer ratio for multi-solution based bone cements with cross-linked PMMA beads. Solutions had a constant ratio in the concentration of cross-linked beads to linear PMMA. As expected, viscosity increases significantly with increasing P:M ratio. The addition of cross-linked PMMA beads allows for a nearly double P:M ratio compared to standard two-solution (TS) cements with comparable solution viscosity. The viscosity of Simplex P commercial bone cement has been reported as 800 Pa*s at 3 min after the onset of mixing. This data also demonstrates that the P:M ratio of these cements can be nearly doubled as compared to standard two-solution cements, while maintaining a comparable viscosity.

The polymerization exotherm measured for multi-solution bone cement with cross-linked PMMA beads was significantly lower than that of standard two-solution cement with the same initiation chemistry and comparable to the commercially available Palacos R-40 bone cement. There were no significant differences in setting times across the three compositions. These data are for a single cement composition with a P:M ratio of 1.4:1. The polymerization exotherm in setting bone cement is inversely proportional to the P:M ratio, therefore, it is reasonable to expect that a further reduction in exotherm could be achieved by increasing the P:M ratio to the range of 1.7:1, which is certainly feasible from a viscosity standpoint, see FIG. 2.

Table 1 below provides the exotherm and setting time for multi-solution based cement with cross-linked beads, standard two-solution cement, and Palacos R-40 commercial cement. Values are given as the average±one standard deviation and significant differences (p<0.05) are denoted by asterisks.

TABLE 1

|  | Palacos R-40 | Two-solution | multi-solution w/beads | |
|---|---|---|---|---|
| P:M    $P_b:P_l$ | 1.71:1 | 0.9:1 | 1.4:1 | 1.8:1 |
| $T_{max}$ (° C.) | 81.18 ± 5.99 | 95.012 ± 5.75* | 75.97 ± 0.94 | |
| $t_{set}$ (min) | 8.48 ± 0.31 | 8.73 ± 0.52 | 9.175 ± 0.12 | |

Figure 3:
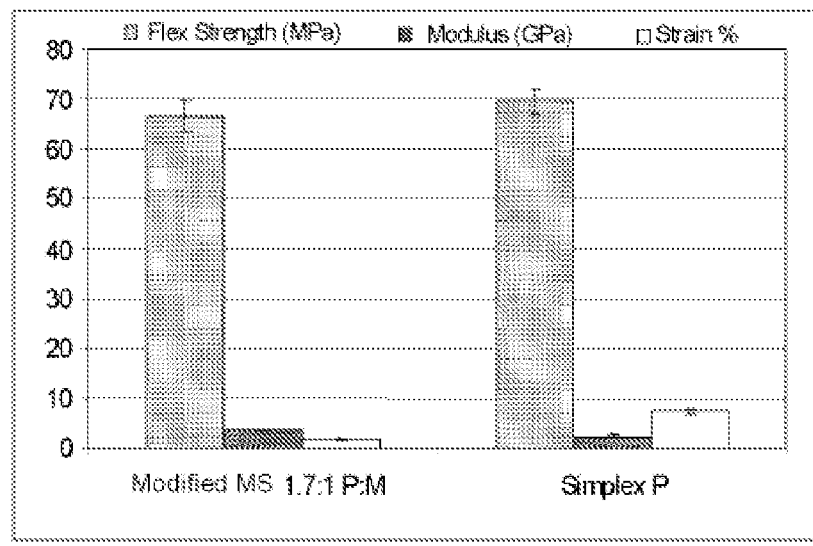
FIG. 3 is a graph of flexural testing data for multi-solution bone cements according to an embodiment of the present invention.

As seen in FIG. 3, in a preliminary investigation of the flexural mechanical properties of multi-solution based bone cements with cross-linked PMMA beads, this type of cement displays comparable flexural strength to Simplex P bone cement. FIG. 3 provides flexural testing data showing flexural strength, modulus, and strain-to-failure for one composition of multi-solution based bone cement with cross-linked PMMA beads at a P:M ratio of 1.7:1 and Simplex P bone cement. There is a significant reduction in the strain-to-failure for the multi-solution based cement.

Figure 4:
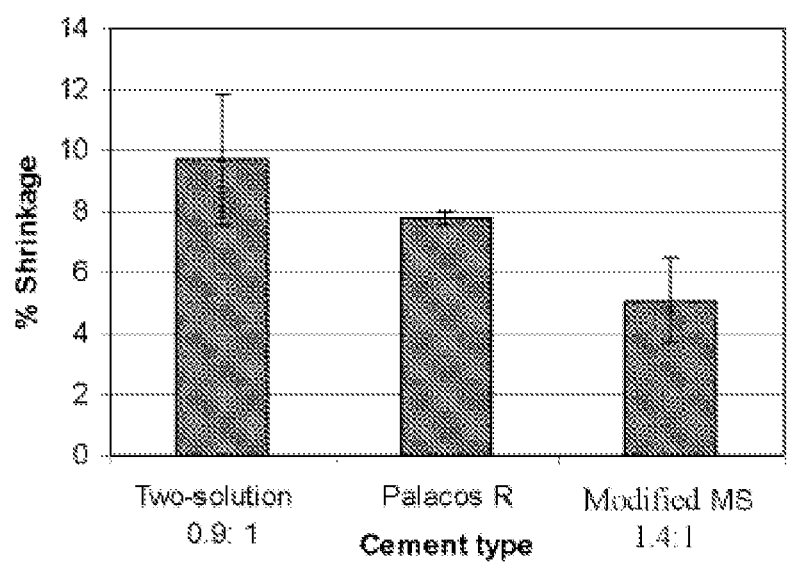
FIG. 4 is graph of volumetric shrinkage verses bone cement composition according to an embodiment of the present invention.

Referring to FIG. 4, tests measuring the volumetric shrinkage of bone cement during the polymerization process show that multi-solution based bone cement with cross-linked PMMA beads at a P:M ratio of 1.4:1 had significantly reduced shrinkage versus standard two-solution cement and Palacos R-40 bone cement. FIG. 4 depicts volumetric shrinkage versus cement composition. Increasing the P:M ratio of multi-solution bone cement via the addition of cross-linked PMMA beads reduced the volumetric shrinkage of the cement, which is due to the conversion of monomer to polymer. This data demonstrates another cement property for which an increase in the P:M ratio is beneficial.

Example 4

Surface Modification of PMMA Cross-Linked Beads

This example relates to the surface modification of PMMA cross-linked beads as synthesized in Example 1. The bead-matrix interface can be mechanically strengthened by promoting covalent bonding between the two phases. Therefore, cross-linked PMMA beads have been modified to create unsaturated carbon double bonds at their surface. These double bonds can participate in the free radical polymerization reaction during matrix formation, potentially creating a chemical bond at the bead-matrix interface.

Step One: Surface Modification of PMMA Beads with Ethanolamine

Figure 5:
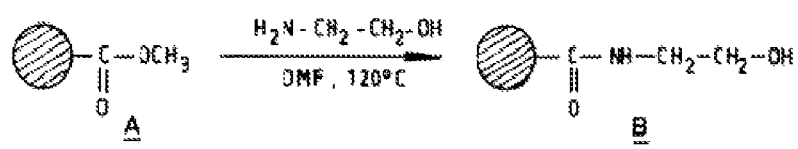
FIG. 5 is a reaction schematic of PMMA with ethanolamine in DMF according to an embodiment of the present invention.
Figure 6:
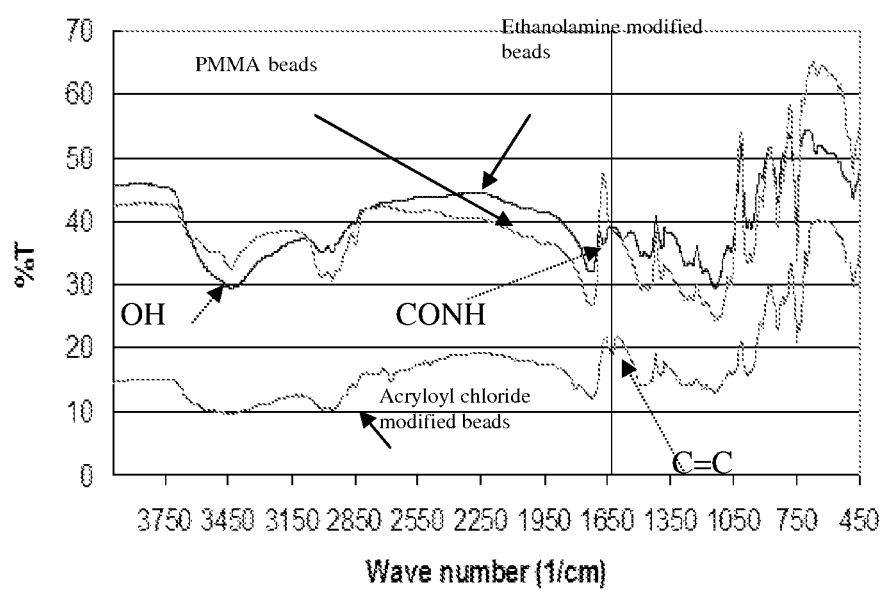
FIG. 6 is a graph of FTIR profiles in transmission mode of the modification reactions according to an embodiment of the present invention.

The first step in the formation of modified PMMA beads according to the invention is to modify the surface of PMMA beads by adding a hydroxyl group. This reaction replaces the ester group with a hydroxyl group, as shown in FIG. 5. The reaction was performed at 120° C. in N,N dimethylformamide (DMF). Twenty grams of cross-linked PMMA beads were swollen for 12 hours in DMF. Then the beads were subjected to a reaction with 25 g of ethanolamine at 120° C. for 9 hours. The reaction was then cooled to ambient temperature. The beads were washed with water, followed by methanol. Finally, the beads were subjected to soxholet extraction with methanol for 48 hours to extract any ethanolamine residue. FTIR analysis of the beads was performed by incorporating the modified beads in a potassium bromide (KBr) pellet. FIG. 6 contains three lines starting from the left (related to each other relative to the vertical axis) including a "top," "middle," and "bottom" line or spectrum. FIG. 6 illustrates the FTIR spectra of cross-linked PMMA beads (middle spectrum) and ethanolamine surface modified PMMA beads (top spectrum). FIG. 6 details the FTIR profiles in transmission mode of the two step modification reactions. The middle line shows the spectrum of the unmodified cross-linked PMMA beads. The top line shows the spectrum of ethanolamine modifies beads. The bottom line shows the spectrum of acryloyl modified beads. Note the carbon-carbon double bond peak at $\approx 1640$ cm$^{-1}$. The hydroxyl group is very clear at 3450 cm$^{-1}$ and amide group at 1680 cm$^{-1}$. These two peaks increase in intensity with increasing reaction time or decreasing cross-linker concentration.

Step Two: Surface Modification with Acryloyl Chloride

Figure 7:
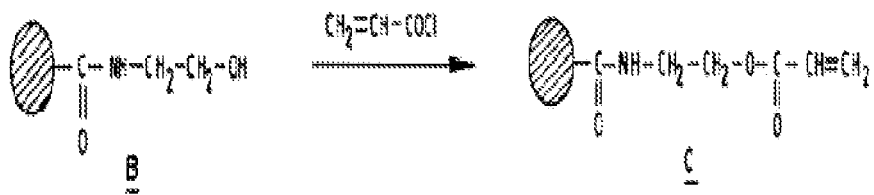
FIG. 7 is a reaction schematic of modified PMMA beads with acryloyl chloride in dimchloromethane according to an embodiment of the present invention.

The second step in the formation of modified PMMA beads according to the invention is to subject the ethanolamine modified cross-linked PMMA beads to acryloyl chloride in dry dichloromethane in the presence of triethylamine, as seen in FIG. 7. Five grams of cross-linked PMMA beads were swollen in 25 g of dry dichloromethane and cooled on ice under stirring. The reaction was permitted to go for 6 hours at 0° C. and then for another 6 hours at room temperature. The product was then washed with 0.1 N HCl followed by saturated sodium hydrogen carbonate solution, followed by water, and finally methanol. The product was dried in a vacuum at room temperature. FIG. 6 shows the FTIR spectrum of acryloyl chloride modified beads (bottom line) in KBR pallets. Note the drop in the hydroxyl peak at 3450 cm$^{-1}$ and the formation of the carbon-carbon double bond peak at 1640 cm$^{-1}$.

Example 5

Preparation of Multi-Solution Bone Cement with Surface Modified PMMA Beads

This Example relates to the preparation of multi-solution bone cement with the surface modified PMMA as synthesized in Example 4. The formation of modified PMMA beads according to the invention also requires determining the desired ratio of surface modified, cross-linked beads to PMMA powder (linear chains). These two components are massed and subsequently mixed together in a suitable container. Next, MMA is added to two graduated cylinders. The desired concentration of BPO initiator or DMPT activator is then dissolved in the MMA, followed by the addition of 10-30 wt % barium sulfate (if radiopacity is desired). The solutions are transferred to 200 ml polypropylene cartridges. Next, the mixture of PMMA powder and surface modified, cross-linked PMMA beads is added to the MMA solutions. The cartridges are sealed, vigorously agitated by hand, and placed on a rotating drum mixer for 6 hours. Following mixing, the cartridges are removed and stored upright at 4° C. The solutions can be mixed through a static mixing nozzle and polymerize in the same manner as multi-solution bone cement without cross-linked beads.

Example 6

Synthesis of PMMA-PMMA Spherical Polymer Brushes

Figure 8:
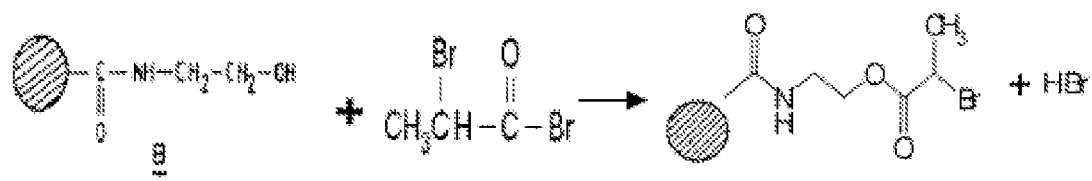
FIG. 8 is a reaction schematic of a modification reaction according to an embodiment of the present invention.

This Example relates to the synthesis of PMMA-PMMA spherical polymer brushes. The synthesis of the polymer brushes of the present invention is performed by surface modification of PMMA beads with ethanolamine as previously described in Example 4, followed by modification with 2-bromoisobutyryl bromide and finally an atom transfer radical polymerization (ATRP) reaction with MMA. Surface modification with 2-bromoisobutyryl bromide was performed on ethanolamine modified PMMA beads in THF at 0° C. in the presence of triethylamine for 12 hrs. This reaction was continued for 24 hours at room temperature followed by filtrations, cleaning and finally drying in a vacuum at room temperature. FIG. 8 is a schematic of the reaction between ethanolamine modified PMMA beads and 2-bromoisobutyryl bromide.

Figure 9:
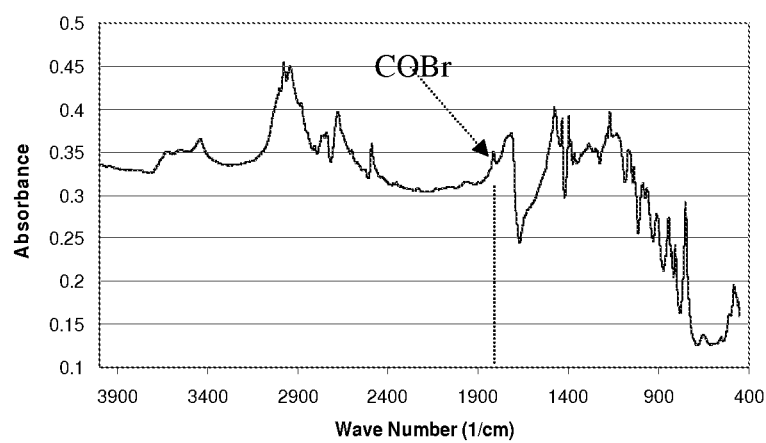
FIG. 9 is a graph of the FTIR profile of 2-bromopropionyl bromide modified PMMA beads according to an embodiment of the present invention.

FTIR analysis in a KBr disk was performed on the modified beads to confirm the surface modification. FIG. 9 shows the FTIR profile of 2-bromoisobutyryl bromide modified cross-linked PMMA beads, where the peak at 1813 cm$^{-1}$ is the COBr peak. Note the drop in the hydroxyl peak and the appearance of COBr at 1813 cm$^{-1}$ and 1168 cm$^{-1}$.

Atom Transfer Radical Polymerization (ATRP)

Atom transfer radical polymerization (ATRP) reaction was carried out in a Schlenk flask at room temperature for 24 hours in the presence of surface brominated PMMA beads, Cu(I)Br, Cu(II)Br, hydroquinone free MMA, and hexamethyl triethylene triamine. The product of the reaction was cleaned thoroughly, then weighed and imaged. Before the ATRP reaction, PMMA modified beads were 100 micron or less in diameter. Bead diameter increased after the reaction to as much as 200 microns. In addition, the weight of the beads was measured before and after the reaction. The weight increased by 200%.

Example 7

Preparation of Bone Cement with PMMA-PMMA Spherical Brushes

This Example relates to the preparation of bone cement with PMMA-PMMA spherical brushes as synthesized in Example 6. The preparation of the third type of cement according to the present invention differs from the procedures for the first two types in that the polymer brushes will be the only solid polymer component added to the MMA, initiation chemicals, and radiopacifier in order to form the cement solutions (i.e., no linear polymer is dissolved).

One or more of the multi-solution bone cements according to the present invention have the capacity to meet the clinical need of improved cements for fixation of total joint replacements, along with other applications including vertebroplasty (VP) and kyphoplasty (KP) which are minimally invasive procedures used to treat vertebral compressive fractures. The change in form of cement, from powder-liquid to multi-solution based, significantly simplifies the mixing and delivery procedure in the operating room and produces a cement of more consistent quality, by eliminating variability in these processes. The multi-solution bone cements according to the present invention also have well controlled viscosities which remain relatively constant during the mixing and delivery process, as opposed to the viscosity of current commercial cements which is highly dynamic and increases significantly from the point of mixing to implantation of the cement. This property is particularly desirable for VP and KP applications.

Example 8

This example describes the effect of overall polymer-to monomer ratio (P:M) and polymer bead (Pb) to linear polymer (Pl) ratio on the viscosity of modified multi solution bone cements.

Cross-linked polymer beads were synthesized. These beads consisted of 12% crosslinker with a nominal bead size of about 20 to 50 µm. These were made using suspension polymerization methods. Then, multi-solution bone cements were made with MMA monomer, 80,000 g/mol molecular weight linear PMMA polymer and the cross-linked PMMA beads. Various ratios of bead to linear polymer and total polymer to monomer were fabricated and their viscosity was determined using rheometric methods at room temperature. The ranges were: P:M ratio of 1.3:1 to 1.4:1, and Pb:Pl ratio of 1:1 to 2.5:1.

Figure 10:
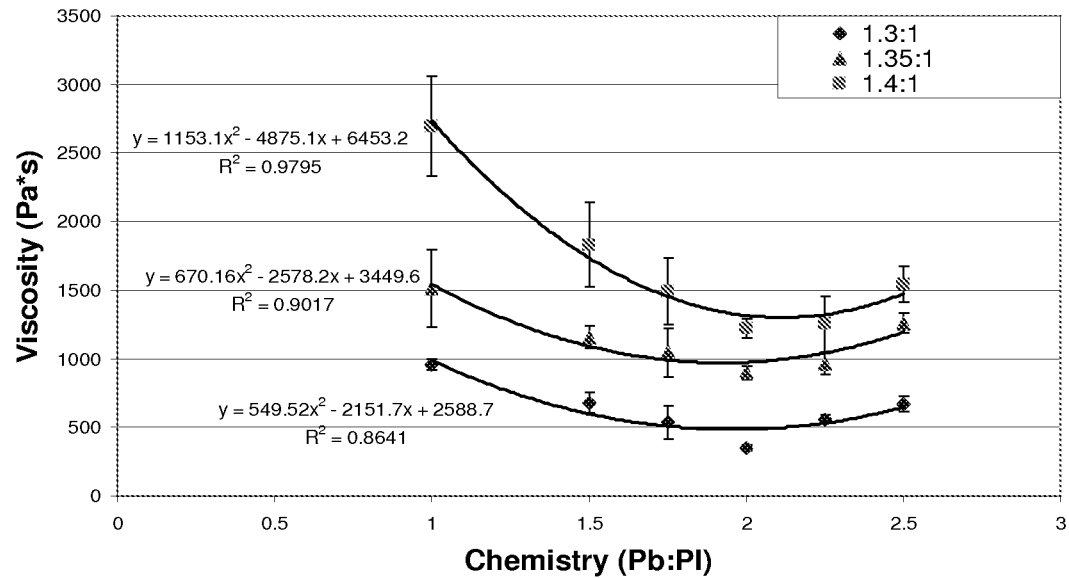
FIG. 10 is a graph of a summary of viscosity versus Pb:Pl ratio for three different P:M ratio multi-solution bone cements according to an embodiment of the present invention.

The results of viscosity testing are summarized in FIG. 10, which shows a summary of viscosity versus Pb:Pl ratio for three different P:M ratio multi solution bone cements. Note that the viscosity decreases with decreasing P:M ratio, and that increasing Pb:Pl ratio first decreases viscosity (below 2:1) and then slightly increases (above 2:1) viscosity.

It can be seen that the viscosity of the cement varies both with bead-to-linear-polymer ratio as well as polymer to monomer ratio. There is an increase in viscosity with increasing P:M ratio at every fixed Pb:Pl ratio. There is also a very interesting change in viscosity with ratio of bead polymer to linear polymer. There is a decrease, then slight increase in viscosity is the quantity of bead polymer is increased relative to linear polymer with a distinct minimum occurring at about 2:1 for all three P:M ratio cases. This indicates that the viscosity will decrease as the amount of bead polymer increases up to the 2:1 ratio. Above this ratio, increasing the Pb:Pl ratio slightly raises the viscosity and eventually the viscosity levels out (data not shown). These changes appear to reflect complex viscosity behavior where at less than the 2:1 ratio, the beads interfere with the mechanism of viscosity formation (primarily linear polymer chain sliding) and reduce the overall viscosity, whereas above 2:1, the viscosity increases as the bead-bead interactions begin to create increased viscosity.

This example shows that viscosity of multi-solution bone cement can be modified by the presence of cross-linked polymer beads, and that a minimum viscosity condition is developed at a ratio of Pb:Pl of around 2:1.

Example 9

This Example shows the mechanical properties of modified multi solution bone cement made from cross-linked polymer beads, linear polymer and monomer after the cements have been polymerized as they would be in-vivo.

Modified multi solution bone cements consisting of linear 80,000 g/mol polymer, cross-linked polymer PMMA beads (with 12% EGDMA cross linker), MMA monomer and BPO and DMPT were used to make polymerized solid cement samples for mechanical testing. The Multi-solution mixtures were dispensed through a static mixing nozzle into rectangular Teflon molds approximately 3 mm×10 mm×40 mm. These samples were then used in three point bending flexural testing to determine the flexural strength (i.e., the stress to cause failure in 3-point bending), flexural modulus (E) and flexural strain to failure. The samples, once fabricated were measured and then tested on a mechanical test frame until failure. The stress, strain and modulus were determined using the standard equations for 3-point bending.

Figure 11A:
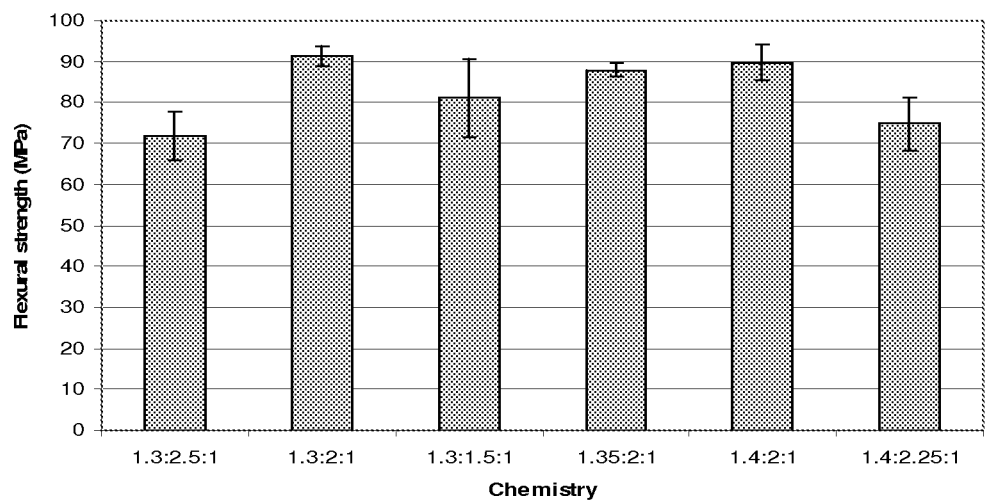
FIG. 11 shows the stress to failure, the strain to failure and the modulus of modified multi-solution bone cements according to an embodiment of the present invention.
Figure 11B:
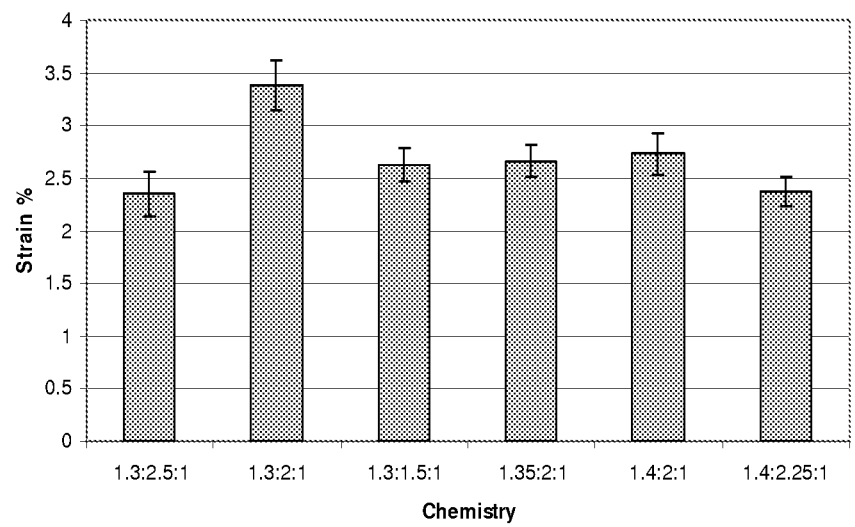
Figure 11C:
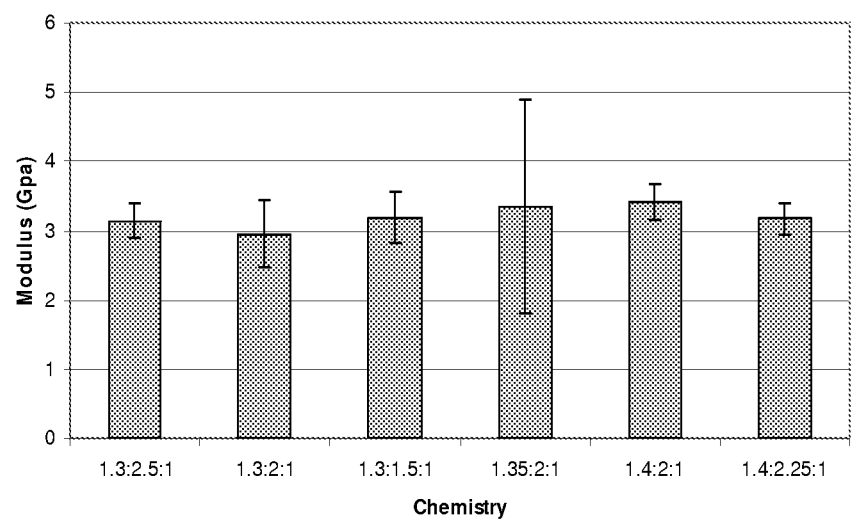

The results are shown in FIG. 11 (11A-11C). Shown are the stress to failure, the strain to failure and the modulus. The x-axis nomenclature is such that the first number is the P:M ratio and the second set of numbers are the Pb:Pl ratio. For example, 1.3:2.5:1 means P:M ratio of 1.3:1 and Pb:Pl of 2.5:1. The results show that for a variety of combinations, the strength of the resulting polymerized cements ranges from 70 MPa to 90 MPa, the strain to failure ranges from 2.3 to 3.3 and the modulus is in the range of 3 GPa. All of these values are in the range of current commercial powder-liquid cements.

While several embodiments of the invention have been discussed, it will be appreciated by those skilled in the art that various modifications and variations of the present invention are possible. Such modifications do not depart from the spirit and scope of the invention.

What is claimed is:

1. A multi-solution bone cement comprising:
   a first solution comprising a mixture of an initiator, a linear polymer, cross-linked beads, wherein said cross-linked beads comprise cross-linked poly(methyl methacrylate) (PMMA) beads, wherein a surface of each of said cross-linked beads comprise functional reactive sites, and wherein said functional reactive sites comprise carbon-carbon double bonds, and a monomer;
   a second solution comprising a mixture of an activator, said linear polymer, said cross-linked beads, and said monomer; and
   wherein said cross-linked PMMA beads comprising said functional reactive sites comprise the following formula:

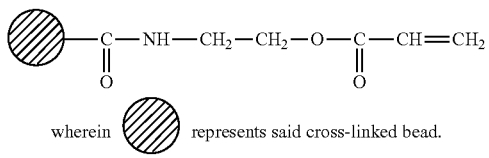

wherein represents said cross-linked bead.

2. A method of forming a multi-solution bone cement system,
   comprising the steps of:
   synthesizing cross-linked beads;
   mixing said cross-linked beads with a linear polymer to form a first mixture;
   mixing a monomer with a first initiator to form a second mixture;
   mixing said first mixture and said second mixture in a first container to form a first solution;
   mixing said cross-linked beads with said linear polymer to form a third mixture;
   mixing said monomer with an activator to form a fourth mixture;
   mixing said third mixture and said fourth mixture in a second container to form a second solution;
   sealing said containers and mixing said solutions within said containers; and
   storing said containers;
   wherein said cross-linked beads comprise cross-linked poly(methyl methacrylate) (PMMA) beads, wherein a surface of each of said cross-linked beads comprise functional reactive sites, wherein said functional reactive sites comprise carbon-carbon double and wherein said cross-linked PMMA beads comprising said functional reactive sites comprise the following formula:

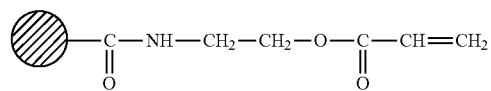

wherein represents said cross-linked bead.

3. The method of claim 2, wherein said linear polymer comprises poly(methyl methacrylate) (PMMA).

4. The method of claim 3, wherein said monomer comprises methyl methacrylate monomer (MMA).

5. The method of claim 2, wherein the step of synthesizing said cross-linked PMMA beads further comprises the steps of:
   performing suspension polymerization of MMA using a second initiator, a cross-linker and a stabilizer, wherein said suspension polymerization forms resulting cross-linked PMMA beads; and
   subjecting said resulting cross-linked PMMA beads to post-synthesis heat treatment.

6. The method of claim 5, wherein said first and second initiators are selected from the group consisting of benzoyl peroxide (BPO), 2,2'-azo-bis-isobutyrylnitrile (AIBN), and potassium persulfate (KPS).

7. The method of claim 6, wherein said cross-linker comprises ethylene glycol dimethacrylate (EGDMA).

8. The method of claim 7, wherein said activator comprises N,N-dimethyl-p-toluidine (DMPT).

9. The method of claim 8, further comprising the step of adding radiopaque material to said first and to said second solutions, wherein said radiopaque material is selected from the group consists of barium sulfate and $ZrO_2$.

* * * * *